United States Patent [19]
Hitomi et al.

[11] Patent Number: 6,001,103
[45] Date of Patent: Dec. 14, 1999

[54] BONE CONNECTOR

[75] Inventors: Shigeki Hitomi, Osaka-fu; Hiroshi Mizuno, Kyoto-fu; Satoshi Ojima; Katsuki Hayashi, both of Tokyo, all of Japan

[73] Assignee: Asahi Kogaku Kogyo Kabushiki Kaisha, Tokyo, Japan

[21] Appl. No.: 09/044,257

[22] Filed: Mar. 19, 1998

Related U.S. Application Data

[62] Division of application No. 08/757,725, Nov. 26, 1996, abandoned, which is a division of application No. 08/396,577, Mar. 1, 1995, Pat. No. 5,643,267, which is a continuation of application No. 08/028,196, Mar. 9, 1993, abandoned.

[30] Foreign Application Priority Data

Mar. 10, 1992 [JP] Japan ................................. 4-87756
May 21, 1992 [JP] Japan ................................ 4-155754

[51] Int. Cl.⁶ .................................................. A61B 17/86
[52] U.S. Cl. ............................................. 606/73; 411/383
[58] Field of Search ........................ 606/72, 73; 411/383, 411/389, 508, 509, 913

[56] References Cited

U.S. PATENT DOCUMENTS

| | | |
|---|---|---|
| 64,654 | 5/1867 | Floyd . |
| 428,063 | 5/1890 | Boda . |
| 432,626 | 7/1890 | Killinger . |
| 1,644,477 | 10/1927 | Klaus . |
| 1,897,196 | 2/1933 | Hunt . |
| 3,488,779 | 1/1970 | Christensen . |
| 4,016,874 | 4/1977 | Maffei et al. . |
| 4,059,041 | 11/1977 | Hassan . |
| 4,158,895 | 6/1979 | Reswick et al. . |
| 4,456,005 | 6/1984 | Lichty . |
| 4,467,794 | 8/1984 | Maffei et al. . |
| 4,682,590 | 7/1987 | Kothmann . |
| 4,726,705 | 2/1988 | Gomes . |
| 4,798,585 | 1/1989 | Inoue et al. . |
| 4,898,493 | 2/1990 | Blankenburg . |
| 4,938,768 | 7/1990 | Wu . |
| 4,946,378 | 8/1990 | Hirayama et al. . |
| 4,969,913 | 11/1990 | Ojima . |
| 5,074,879 | 12/1991 | Pappas et al. . |
| 5,108,398 | 4/1992 | McQueen et al. . |
| 5,128,146 | 7/1992 | Hirayama et al. . |
| 5,147,361 | 9/1992 | Ojima et al. . |
| 5,169,400 | 12/1992 | Muhling et al. . |
| 5,346,501 | 9/1994 | Regula et al. . |

FOREIGN PATENT DOCUMENTS

| | | | |
|---|---|---|---|
| 472727 | 4/1951 | Canada . | |
| 43 07 540 A1 | 9/1993 | Germany | ................................. 606/73 |
| 584029 | 1/1977 | Switzerland . | |
| 1105198 | 7/1984 | U.S.S.R. | .................................. 623/18 |
| 1667854 | 8/1991 | U.S.S.R. . | |
| 1692566 | 11/1991 | U.S.S.R. . | |

*Primary Examiner*—David H. Willse
*Attorney, Agent, or Firm*—Greenblum & Bernstein, P.L.C.

[57] ABSTRACT

Bone connector including a first joint and a second joint insertable and securable into respective cut bone pieces for joining the cut bone pieces. Each joint has a flat end surface flush with the cut end of the corresponding cut bone piece when secured therein. The first joint includes a stepped hole having a coaxial hole portion, a shoulder with a surface substantially perpendicular to the longitudinal direction of the joints, and an innermost engaging portion. The second joint includes a stepped shaft having a first shaft fitting the coaxial hole portion and an engaging portion for engaging the innermost engaging portion of the first joint, which hold the joints coaxially along a line, as well as a plate spring member. The joints both include cylindrical bodies of substantially equal diameter for connecting the cut bone pieces, and at least outer surface portions of the joints are made of a material having a bioactive affinity with the human body or biocompatibility with human tissue. The plate spring member is deformed as it passes the coaxial hole portion and restored to abut the surface of the shoulder perpendicular to the longitudinal direction, for locking the joints and flush connecting the flat end surfaces with each other.

21 Claims, 10 Drawing Sheets

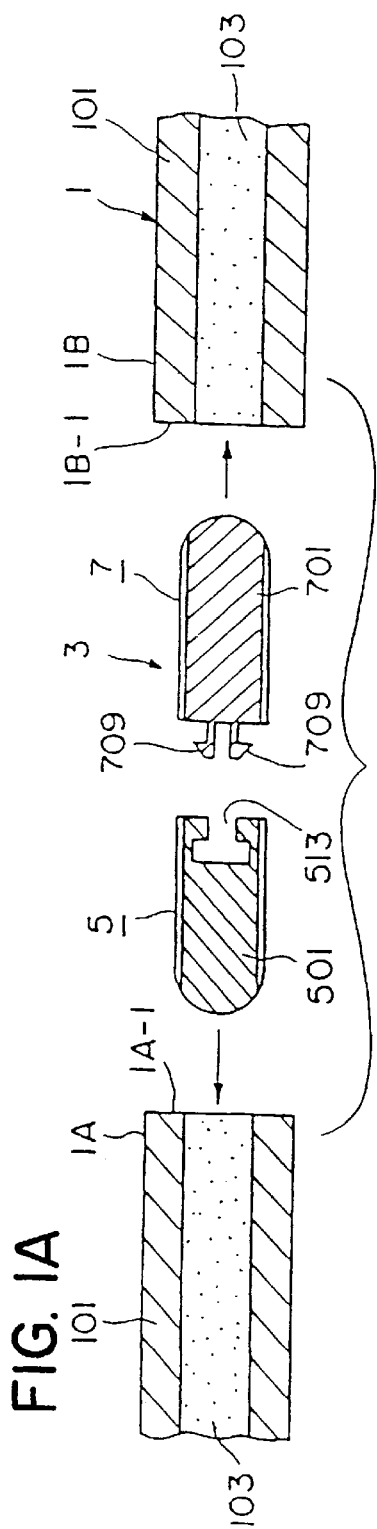
FIG. IA
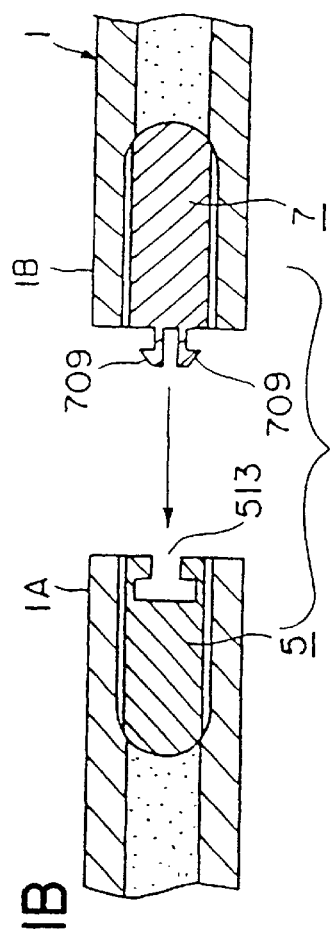
FIG. IB
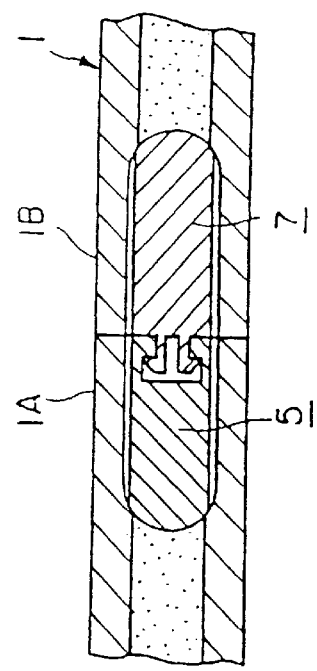
FIG. IC

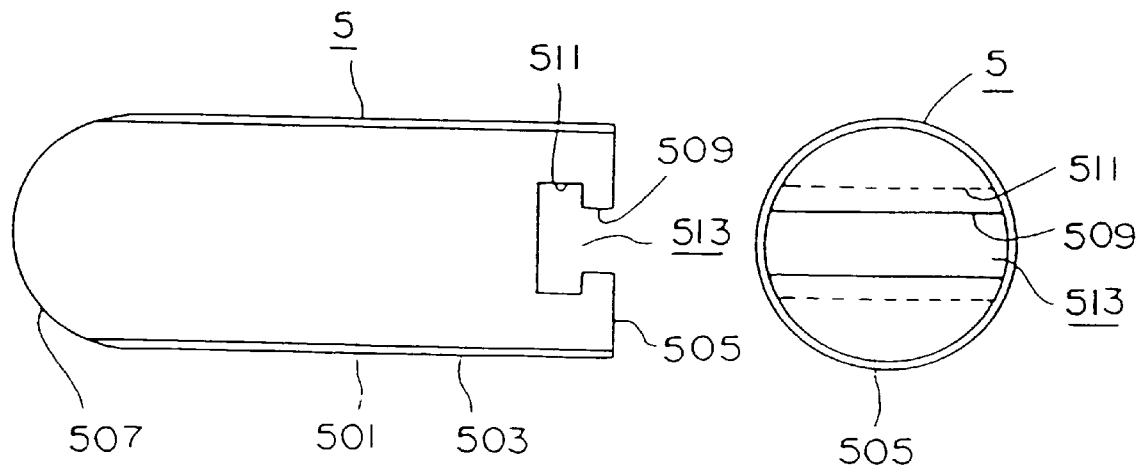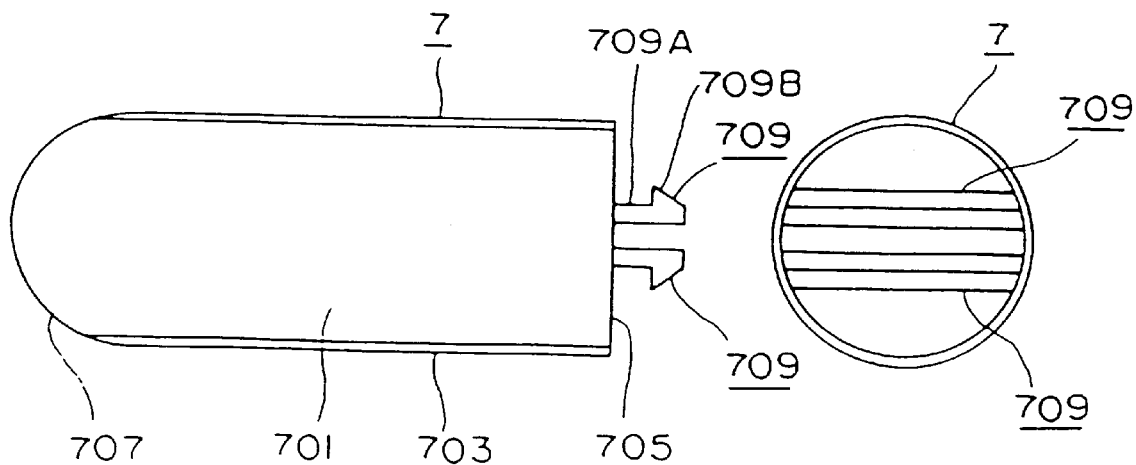

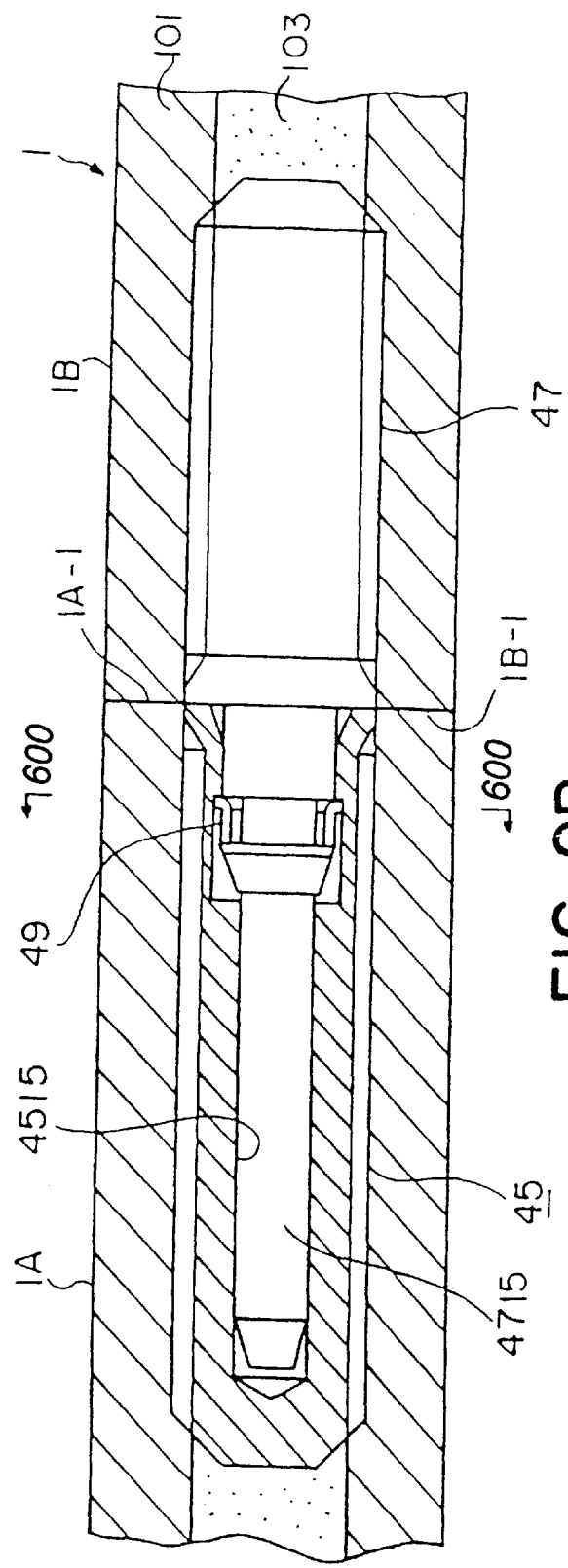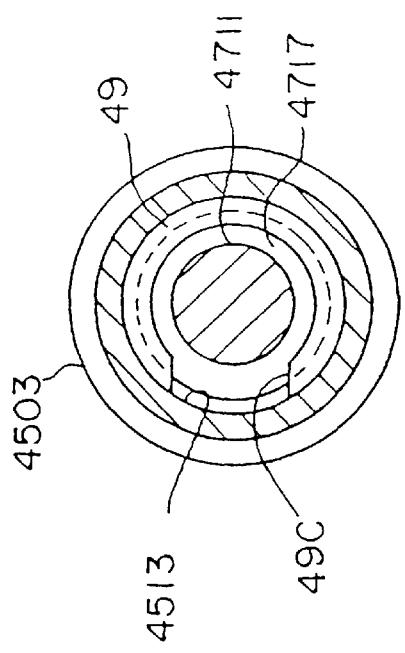

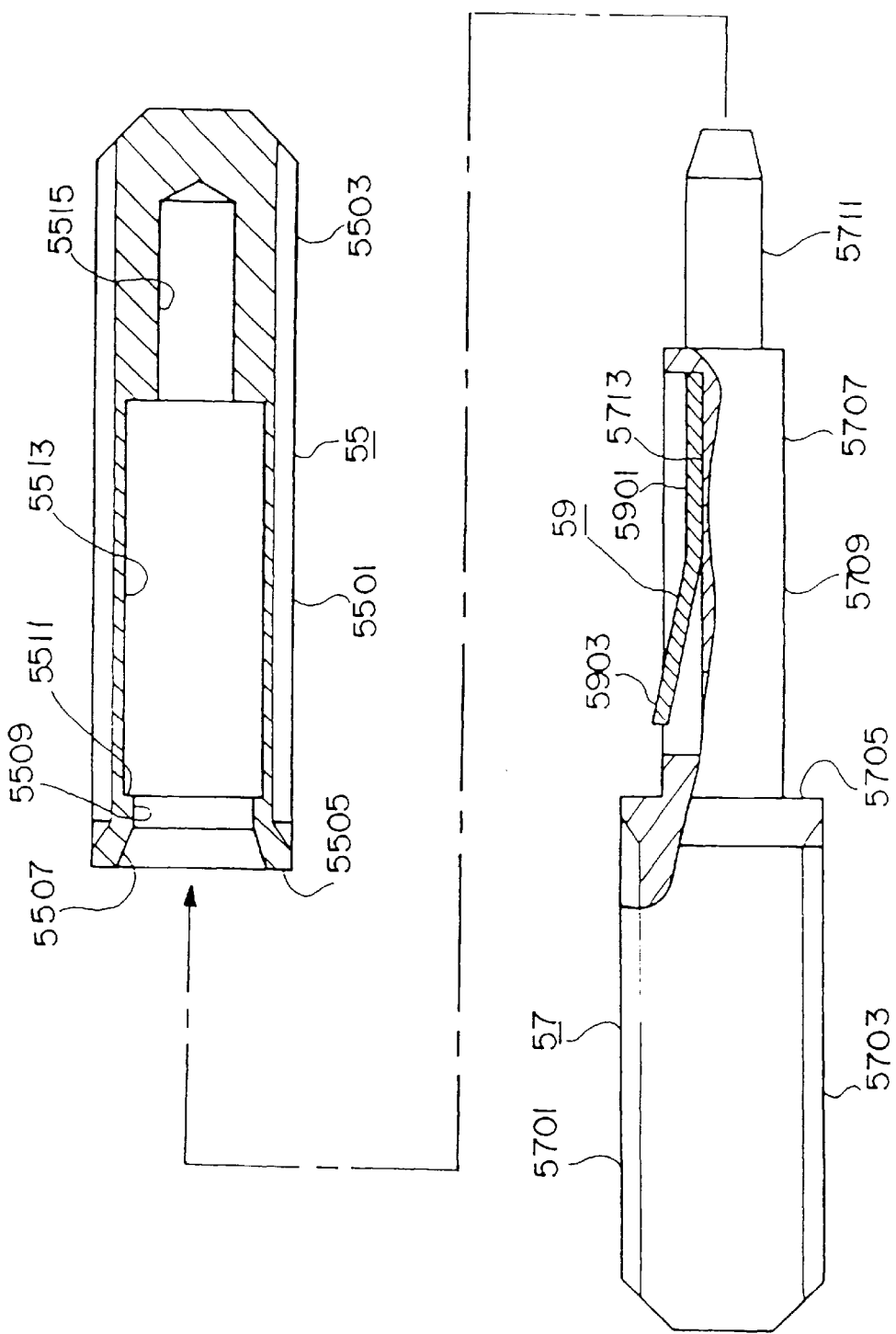

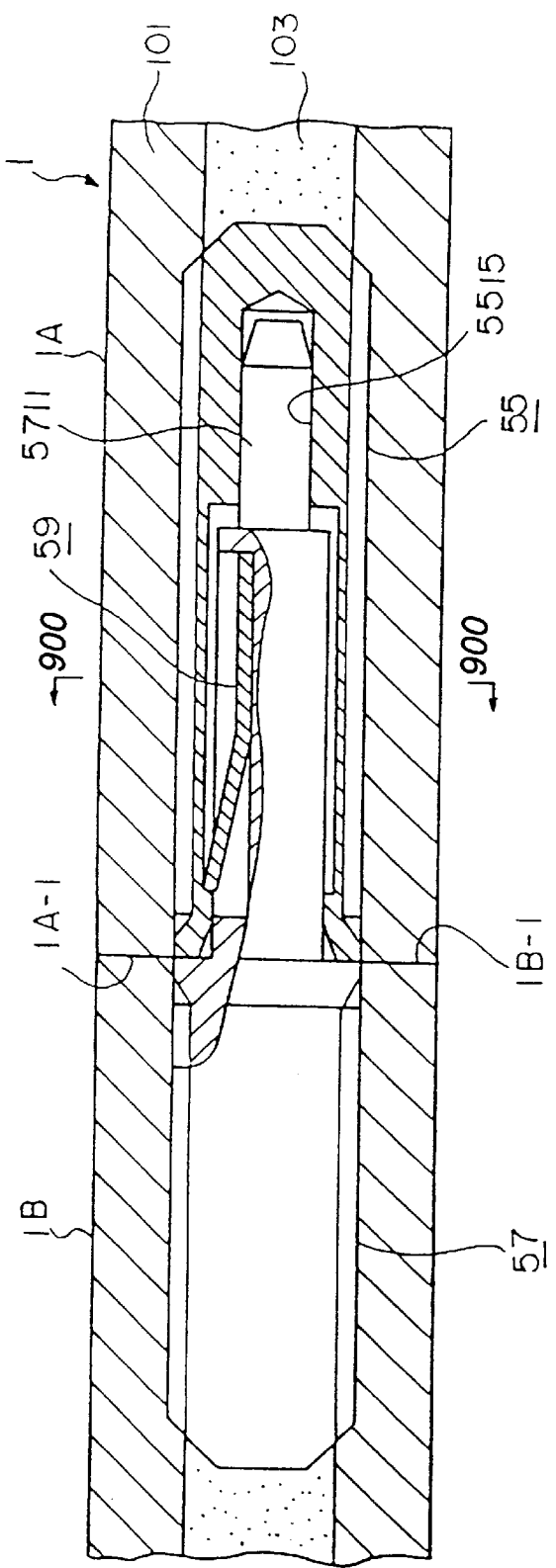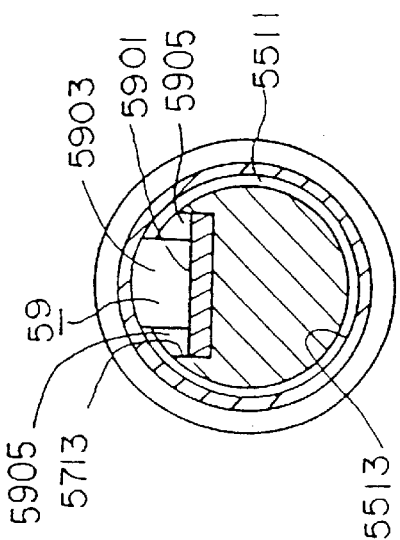

BONE CONNECTOR

This application is a divisional of application Ser. No. 08/757,725, filed Nov. 26, 1996, now abandoned, which is a division of application Ser. No. 08/396,577, filed Mar. 1, 1995, now U.S. Pat. No. 5,643,267, which is a continuation of application Ser. No. 08/028,196, filed Mar. 9, 1993, now abandoned, the contents of which are herein incorporated by reference in its entireties.

BACKGROUND OF THE INVENTION

1. Field of the Invention

The present invention relates to a bone connector which is adapted to connect cut bone pieces.

2. Description of Related Art

For instance, in a surgical operation of the chest including the lungs and the heart, etc., a part of the ribs is usually cut and temporarily removed. After the surgical operation is completed, a piece of bone cut from the rib (referred to as a bone piece) is connected again to the associated rib.

To connect the cut ends of a bone piece and the associated rib, a wire (or biodegradable thread), or a metal or plastic connecting plate is usually used. In the connection using the wire, first, a ceramic pin is inserted in the marrow of the bone piece at the cut end thereof; second, a through hole is pierced in the vicinity of the cut end of the rib. Consequently, the cut end of the rib can be bound by the wire or the thread which is tied to the ceramic pin. The insertion of the ceramic pin and the tying and stringing operations are troublesome, however. Moreover, it is necessary to strip a substantial part of intercostal muscles in the vicinity of the cut ends of the ribs, which burdens a patient during the operation.

In the connection using the metal or plastic connecting plate, holes are pierced in the cut ends of both the bone piece and the associated rib, so that the connecting plate which lies along the outer surfaces of the bone piece and the associated rib is secured to the bone piece and the associated rib by securing pins which are inserted in the connecting plate and the holes of the bone piece and the associated rib to connect the bone piece and the associated rib.

In this method, it is also necessary to strip a substantial part of intercostal muscles in the vicinity of the cut ends of the ribs. Furthermore, the metal plate is heavy, and accordingly, increases the burden on a patient; and the plastic plate has less biocompatibility or bioaffinity with the surrounding tissue of the cut ends of the ribs.

SUMMARY OF THE INVENTION

The primary object of the present invention is to eliminate the drawbacks mentioned above by providing a bone connector which can easily connect the bone ends while minimizing the burden on a patient and which has a good biocompatibility or bioactive affinity with the tissue.

To achieve the object mentioned above, according to the present invention, there is provided a bone connector comprising a first joint which is inserted and secured in the cut end of one of the cut bone pieces to be interconnected, a second joint which is inserted and secured in the cut end of the other cut bone piece to be interconnected, and engaging portions provided on the first and second joints to connect the same.

According to another aspect of the present invention, there is provided a bone connector comprising first and second joints which are secured to cut ends of bone pieces to be interconnected, engaging portions provided on the first and second joints to connect the same, and an elastically deformable spring member which is restored when the engagement of the engaging portions is completed to lock the engagement.

According to still another aspect of the present invention, a bone connector comprises a first joint which is secured to a cut end of one of the bone pieces to be interconnected, and a second joint which is secured to a cut end of the other bone piece, wherein said first joint is provided with a first body which can be embedded and secured in the cut end of said one bone piece, and a first engaging portion provided on the first body; said second joint is provided with a second body which can be embedded and secured in the cut end of said the other bone piece, and a second engaging portion provided on the second body and being engaged by the first engaging portion, so that when the engagement of the first engaging portion and the second engaging portion is established, the cut ends of the bone pieces are held in a close surface contact; said first and second joints are made of a material strong enough to hold a close surface contact of the cut ends of the bone pieces; said first and second bodies are coated at least at the outer surfaces thereof with a material which is assimilative to or has a bioactive affinity with the tissue.

The present disclosure relates to subject matter contained in Japanese patent applications Nos. 4-87756 (filed on Mar. 10, 1992) and 4-155754 (filed on May 21, 1992) which are expressly incorporated herein by reference in their entirety.

BRIEF EXPLANATION OF THE DRAWINGS

The invention will be described below in detail with reference to the accompanying drawings, in which;

FIGS. 1A through 1C are explanatory views of a connecting operation of cut ribs, using a bone connector according to the present invention;

FIGS. 2A and 2B are a side elevation view and a front elevation view of a first joint of a bone connector according to a first embodiment of the present invention, respectively;

FIGS. 3A and 3B are a side elevation view and a front elevation view of a second joint of a bone connector according to a first embodiment of the present invention, respectively;

FIG. 9A is a side elevation view of first and second joints of a bone connector in an assembled state, according to a fourth embodiment of the present invention;

FIG. 9B is a sectional view taken along the line B—B in FIG. 9A;

FIG. 10 is a side elevation view of first and second joints of a bone connector according to a fifth embodiment of the present invention;

FIG. 11A is a side elevation view of first and second joints of a bone connector in an assembled state, according to a fifth embodiment of the present invention; and, FIG. 11B is a sectional view taken along the line B—B in FIG. 11A; and, FIGS. 12A and 12B are a top view and a side elevation view of a spring according to a fifth embodiment of the present invention.

DESCRIPTION OF THE PREFERRED EMBODIMENT

Figure 4A:
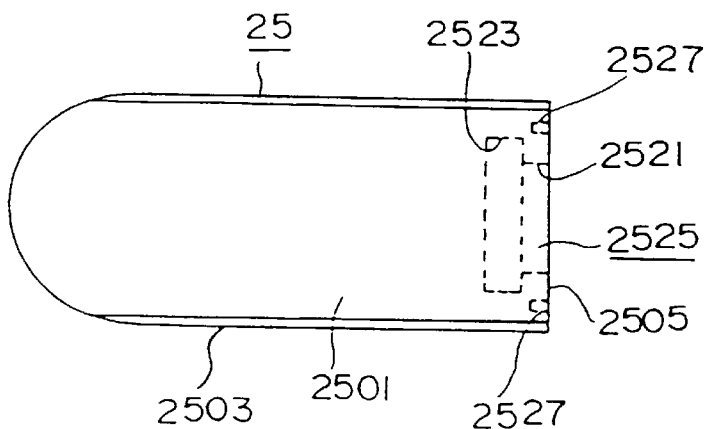
FIGS. 4A and 4B are a side elevation view and a front elevation view of a first joint of a bone connector according to a second embodiment of the present invention, respectively.

FIGS. 1A through 1C illustrate a process for connecting cut rib pieces. A rib 1 is cut at an intermediate portion in a direction perpendicular to the longitudinal axis thereof. One of the cut ribs is indicated at 1A (first bone piece) and the other at 1B (second bone piece). The rib 1 consists of an outer cortex bone portion 101 and a center (inner) marrow 103.

A bone connector 3 according to the present invention includes a first joint 5 which is secured to the cut end of the first bone piece 1A and a second joint 7 which is secured to the cut end of the second bone piece 1B.

The first joint 5 has a circular rod body 501 of predetermined length which is inserted and secured in the first bone piece 1A and which is provided, on the outer peripheral surface thereof, with a thread (male screw) 503, as can be seen in FIGS. 2A and 2B. The rod body 501 has a flat outer end 505 which is flush with the end surface 1A-1 of the first bone piece 1A when the first joint 5 is fitted in the first bone piece 1A, and a semi-spherical inner end 507. The rod body 501 is provided on the outer end 505 thereof, with a stepped engaging groove 513 consisting of a groove 509 of smaller width, and a groove 511 of larger width. The engaging groove 513 extends through the outer end 505 in a direction perpendicular to the longitudinal axis of the rod body 501. In the first embodiment, the engaging groove 513 constitutes an engaging portion of the first joint 5.

The second joint 7 has a circular rod body 701 of predetermined length which is inserted and secured in the second bone piece 1B and which is provided, on the outer peripheral surface thereof, with a thread (male screw) 703, similar to that of the first joint 5, as can be seen in FIGS. 3A and 3B. The rod body 701 has a flat outer end 705 which is flush with the end surface 1B-1 of the second bone piece 1B when the second joint 7 is fitted in the second bone piece 1B, and a semi-spherical inner end 707. The rod body 701 is provided on the outer end 705 thereof, with a pair of engaging projections 709 which can be engaged in the engaging groove 513 of the first joint 5. Each engaging projection 709 has a leg 709A to be fitted into the small groove 509 of the first joint, and a projection 709B which projects from the front end of the leg 709A to be fitted in the large groove 511 of the first joint. In the illustrated embodiment, the engaging projections 709 constitute an engaging portion of the second joint 7.

When the engaging projections 709 of the second joint 7 are fitted in the engaging groove 513 of the first joint 5, the flat end surfaces 505 and 705 of the first and second joints 5 and 7 are flush with each other. The contact is retained by the engagement of the engaging projections 709 and the engaging groove 513.

The first and second joints 5 and 7 are made of, for example, titanium, stainless steel, titanium alloy, etc., and are coated with apatite at the outer surface thereof.

To connect the cut rib 1, i.e., the first and second bone pieces 1A and 1B, the rod body 501 of the first joint 5 is inserted in the marrow 103 and screwed into the cortex bone portion 101 of the first bone piece 1A from the end surface 1A-1, for example, by rotating a screw driver (minus driver) which is fitted in the small width groove 509 of the first joint 5. Similarly, the rod body 701 of the second joint 7 is inserted in the marrow 103 and screwed into the cortex bone portion 101 of the second bone piece 1B from the end surface 1B-1, for example, by rotating a screw driver (minus driver) which is inserted between the engaging projections 709. The first and second joints 5 and 7 are screwed into the first and second bone pieces 1A and 1B until the end surfaces 505 and 705 of the first and second joints 5 and 7 are flush with the end surfaces 1A-1 and 1B-1 of the first and second bone pieces 1A and 1B, respectively, as shown in FIG. 1B. Consequently, the threaded outer peripheral surfaces 503 and 703 of the first and second joints 5 and 7 are screw-engaged in the cortex bone portion 101 of the first and second bone pieces 1A and 1B, so that the first and second joints 5 and 7 are secured to the first and second bone pieces 1A and 1B, respectively.

Thereafter, the first and second bone pieces 1A and 1B are moved towards each other to move the opposed end surfaces 1A-1 and 1B-1 thereof close to each other, so that the engaging projections 709 of the second joint 7 are inserted in the groove 509 of the first joint 5 while being elastically deformed. As soon as the engaging projections 709 of the second joint 7 move past small groove 509 into large groove 511 of the first joint, the engaging projections 709 are restored to their original shape due to elastic restoring force, so that the engaging projections 709 are snugly fitted in the large groove 513. Consequently, the surfaces 505 and 705 of the first and second joints 5 and 7 and the surfaces 1A-1 and 1B-1 of the first and second bone pieces 1A and 1B are flush with each other, respectively, as shown in FIG. 1C.

According to the present invention discussed above, the connecting operation of a pair of bone pieces 1A and 1B can be simplified in comparison with the connection using the wire or biodegradable thread in the prior art. Furthermore, according to the present invention, the separating or stripping of intercostal muscles can be minimized.

The first and second joints 5 and 7 can be made of a material having a rigidity strong enough to retain the close contact of the surfaces of the first and second bone pieces 1A and 1B. Preferably, the first and second joints 5 and 7 are made of a light titanium alloy, so that an artifact is not produced by the bone connector during CT photography. In addition, the joints 5 and 7 made of a light titanium alloy are sufficiently strong, yet sufficiently light to minimize the burden on a patient.

Furthermore, the first and second joints 5 and 7 are coated with apatite, and have no problem with assimilation to or bioactive affinity with the body.

Since the bone tissues of the first and second bone pieces 1A and 1B to be connected come into direct contact with each other, the bone tissues will interconnect easily.

Figure 4B:
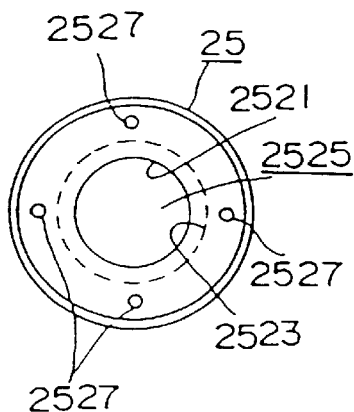
Figure 5A:
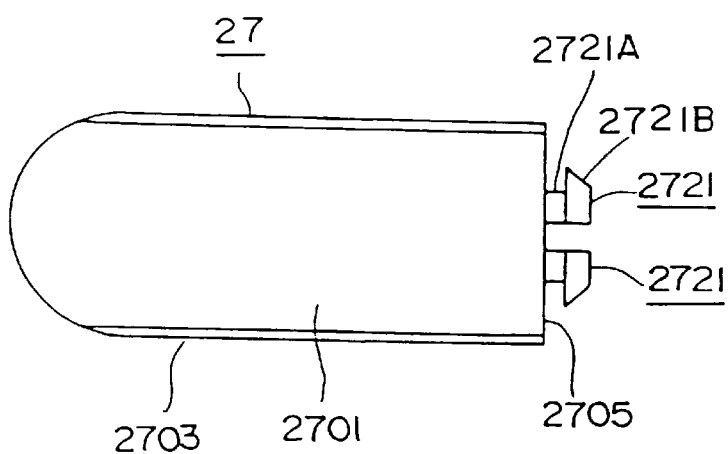
FIGS. 5A and 5B are a side elevation view and a front elevation view of a second joint of a bone connector according to a second embodiment of the present invention, respectively.
Figure 5B:
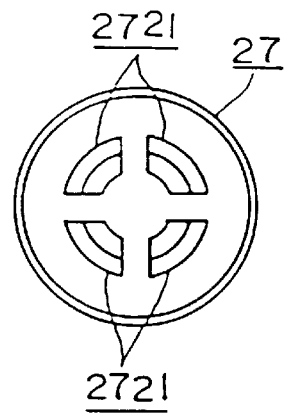

FIGS. 4 and 5 show a second embodiment of the present invention. The engaging grooves and projections of the first and second joints 25 and 27 in the second embodiment differ in shape from those of the first embodiment.

The first joint 25 has a rod body 2501 which is provided on the outer peripheral surface thereof with a threaded portion (male screw) 2503. The rod body 2501 has a flat outer end surface 2505 which is provided with a small diameter center circular recess 2521 and a larger diameter circular recess 2523 which is coaxial to and connected to the center circular recess 2521. The recesses 2521 and 2523 constitute an engaging groove 2525.

The end surface 2505 is provided with four bottomed holes 2527 which are angularly spaced from each other in the vicinity of the outer peripheral surface thereof. A jig or tool which is adapted to screw the first joint 25 into the first bone piece 1A is engaged in the holes 2527.

The second joint 27 has a rod body 2701 which is provided on the outer peripheral surface thereof with a threaded portion (male screw) 2703. The rod body 2701 has a flat outer end surface 2705 which is provided thereon with four engaging projections 2721 which can be fitted in the engaging groove 2525. The engaging projections 2721 are spaced from one another, so that a jig (plus or minus screw driver, etc.) can be fitted therebetween to screw the second joint 27 into the second bone piece 1B.

Each engaging projection 2721 has a leg 2721A to be fitted into the small diameter circular recess 2521 of the first joint and a projection 2721B which projects from the front end of the leg 2721A to be fitted in the larger diameter circular recess 2523 of the first joint.

When the engaging projections 2721 of the second joint 27 are fitted in the engaging groove 2525 of the first joint 25, the flat end surfaces 2505 and 2705 of the first and second joints 25 and 27 are flush with each other. The surface contact is retained by the engagement of the engaging projections 2721 and the engaging groove 2525. Thus, the same technical effects as those in the first embodiment can be expected from the second embodiment.

Figure 6:
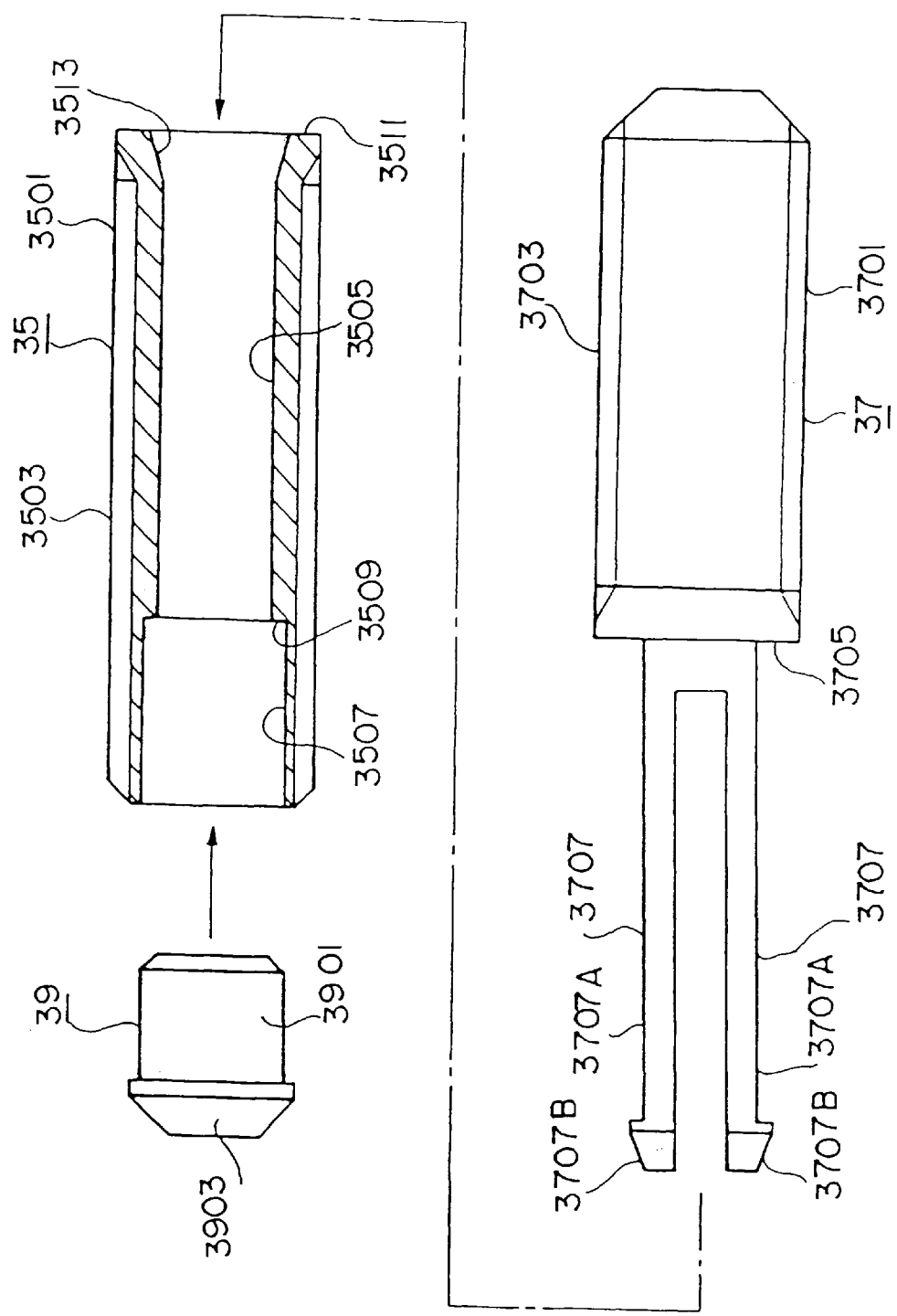
FIG. 6 is a side elevation view of first and second joints of a bone connector according to a third embodiment of the present invention.
Figure 7:
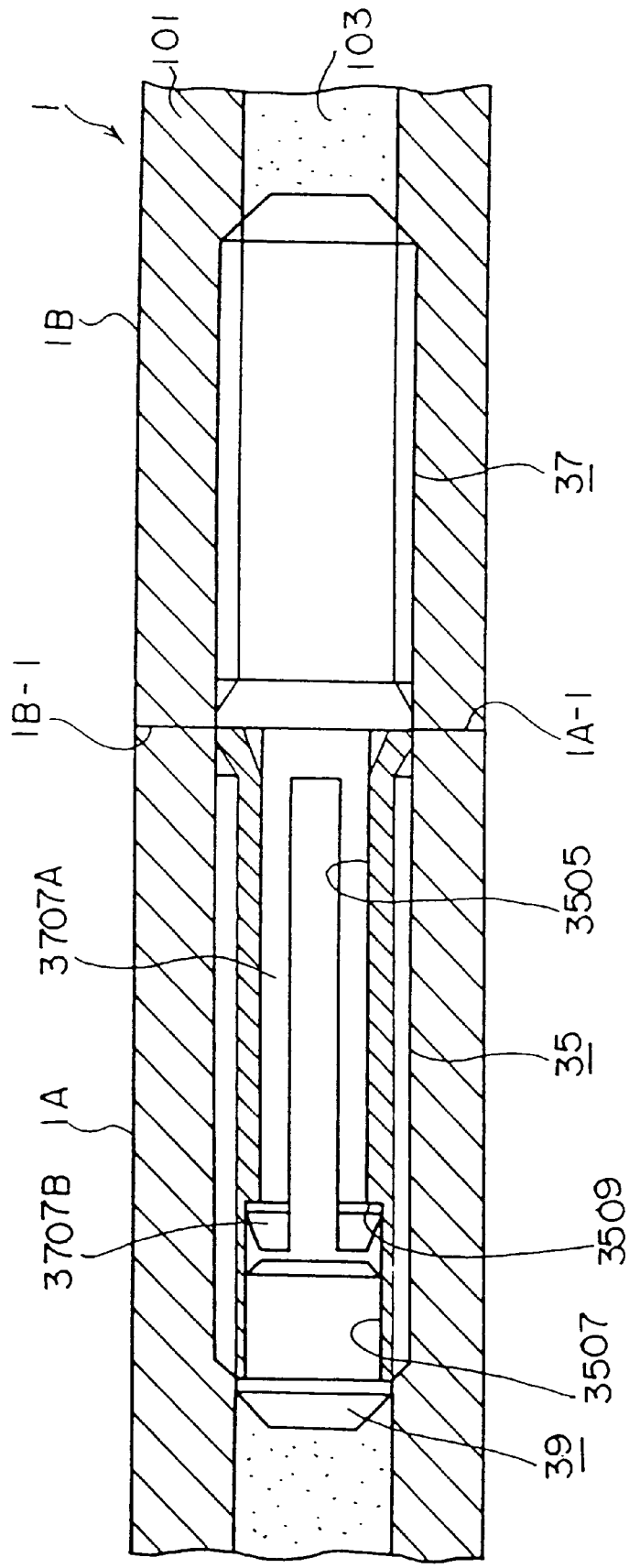
FIG. 7 is a side elevation view of first and second joints of a bone connector in an assembled state, according to a third embodiment of the present invention.

FIGS. 6 and 7 show a third embodiment of the present invention. In the third embodiment, the first joint 35 has a hollow cylindrical body 3501 of predetermined length which is provided on the outer peripheral surface thereof with a threaded portion (male screw) 3503. The hollow portion of the cylindrical body 3501 consists of a small diameter circular hole 3505 and a larger diameter circular hole 3507 coaxial thereto. The small circular hole 3505 and the large circular hole 3507 are connected to each other by a shoulder portion 3509. The small circular hole 3505, the large circular hole 3507, and the shoulder portion 3509 constitute an engaging portion of the first joint 35.

The small diameter circular hole 3505 is provided on the end opposite the shoulder portion 3509, with a conically tapered opening 3513 whose diameter gradually increases towards the open end thereof. The conical opening 3513 terminates at an annular end surface 3511 which is flush with the end surface 1A-1 of the first bone piece 1A when the first joint 35 is correctly inserted in the first bone piece 1A.

The other open end of the large circular hole 3507 is closed by a plug 39 fitted therein. The plug 39 has a circular rod body 3901 to be inserted in the large circular hole 3507 and a head 3903 which abuts against the open end of the cylindrical body 3501 of the first joint 35 when the plug 39 is inserted in the first joint 35. The outer diameter of the head 3903 is substantially identical to or smaller than the root diameter of the thread 3503, as can be seen in FIG. 7. The front end of the head 3903 is tapered in a truncated conical shape.

The second joint 37 has a circular rod body 3701 of predetermined length which is provided on the outer peripheral surface thereof with a threaded portion (male screw) 3703. The rod body 3701 has a flat end surface 3705 which is provided thereon with a plurality of engaging projections 3707. The annular flat end surface 3705 of the rod body 3701 is flush with the flat end surface 1B-1 of the second bone piece 1B when the second joint 37 is fitted in the second bone piece 1B. The other end of the rod body 3701 is conically tapered.

The engaging projections 3707 which are circumferentially spaced from one another can be made of separate pieces or a cylinder or bar which is axially slit in a plurality of radial directions.

Each engaging projection 3707 has a leg 3707A and a projection 3707B which projects from the front end of the leg 3707A. The diameter of an imaginary circle defined by the legs 3707A corresponds to the inner diameter of the small circular hole 3505. The engaging projections 3707 correspond to the engaging portion in the second embodiment.

The dimensions of the circular holes 3505 and 3507 and the shoulder portion 3509 are such that when the legs 3707A are inserted in the small circular hole 3505 while being elastically deformed, and come to the large circular hole 3507, the projections 3707B are snugly fitted in the portion of the large circular hole 3507 that is defined between the plug 39 and the shoulder portion 3509. In this state, the projections 3707B abut against the shoulder portion 3509, and the surfaces 3511 and 3705 of the first and second joints 35 and 37 are flush with each other.

According to the third embodiment shown in FIGS. 6 and 7, in addition to the technical effects achieved by the previous embodiments, the first and second joints 35 and 37 can be coaxially held along a line by the engagement of the legs 3707A and the small circular hole 3505, and accordingly, the first and second bone pieces 1A and 1B can be accurately aligned, thus resulting in an optimal recovery of the ribs.

Figure 8:
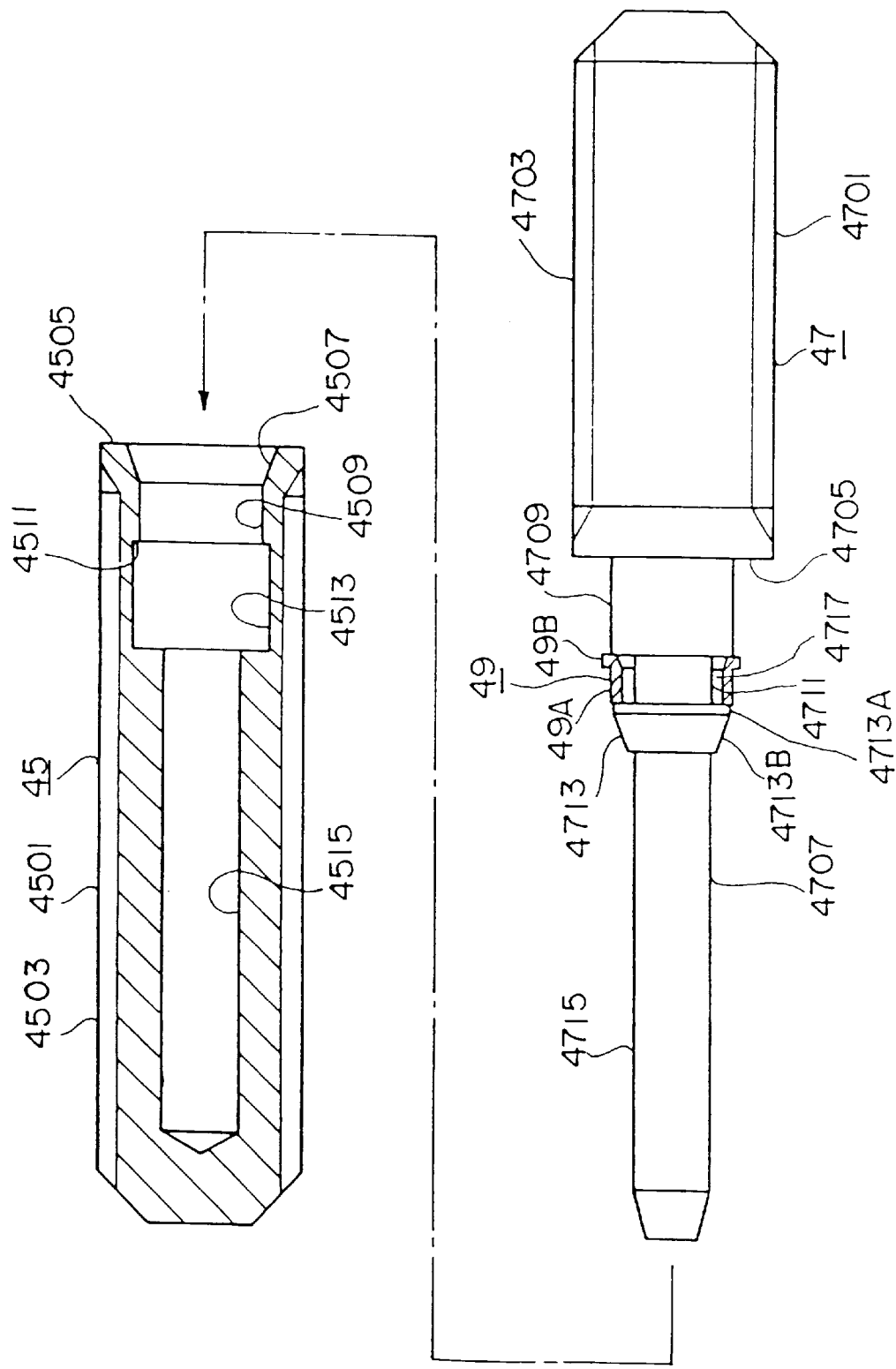
FIG. 8 is a side elevation view of first and second joints of a bone connector according to a fourth embodiment of the present invention.

FIGS. 8 and 9 show a fourth embodiment of the present invention.

The first joint 45 has a bottomed hollow cylindrical body 4501 of predetermined length which is provided on the outer peripheral surface thereof with a threaded portion (male screw) 4503. The cylindrical body 3501 has an annular flat end surface 4505 which is flush with the flat end surface 1A-1 of the first bone piece 1A when the first joint 45 is fitted in the first bone piece 1A. The other end of the first joint 45 is tapered. The cylindrical body 4501 is provided on the open end thereof with a coaxial circular hole 4509 with a tapered opening 4507. The cylindrical body 4501 is also provided therein with a larger diameter circular hole (intermediate circular hole) 4513 which is connected to the small circular hole 4509 through a shoulder portion 4511, and an innermost bottomed circular hole 4515 having a predetermined length (depth) and connected to the intermediate circular hole 4513. The diameter of the innermost circular hole 4515 is smaller than the diameters of the circular holes 4513 and 4509. The circular holes 4509 and 4513 and the shoulder portion 4511 constitute an engaging portion of the first joint 45.

The second joint 47 has a circular rod body 4701 of predetermined length which is provided on the outer peripheral surface thereof with a threaded portion (male screw) 4703. The rod body 4701 has an annular flat end surface 4705 on one end on which a stepped shaft 4707 is provided. The annular flat end surface 4705 of the rod body 4701 is flush with the flat end surface 1B-1 of the second bone piece 1B when the second joint 47 is fitted in the second bone piece 1B. The other end of the rod body 4701 is conically tapered.

The stepped shaft 4707 includes a first shaft portion 4709 which is connected to the flat end surface 4705 and which can be fitted in the circular hole 4509 of the first joint, a second shaft portion 4711 which is connected to the front end of the first shaft portion 4709 and has a diameter smaller than the first shaft portion 4709, a third shaft portion 4713 connected to the front end of the second shaft portion 4711, and a fourth shaft portion 4715 which is connected to the front end of the third shaft portion 4713 and which can be fitted in the circular hole 4515.

The third shaft portion 4713 consists of a cylindrical portion 4713A having a diameter larger than the second shaft portion 4711 and connected to the latter, and a 10 conical portion 4713B connected to the cylindrical portion 4713A. The end face of the cylindrical portion 4713A, the peripheral surface of the second shaft portion 4711, and the end face of the first shaft portion 4709 define an annular recess 4717 in which a spring member 49 is provided. The spring member 49 constitutes an engaging portion of the second joint 47.

The spring member 49 includes a cylindrical portion 49A, a flange portion 49B whose diameter is larger than the diameter of the first shaft portion 4709, and an axial opening (slit) extending through the cylindrical portion 49A and the flange portion 49B, as shown in FIG. 9B. The axial opening 49C permits the spring member to be elastically deformed to contract or expand.

The spring member 49 is preferably made of titanium, stainless steel, a titanium alloy, HDP (high density polyethylene), or high polymer polyethylene, etc.

The dimensions of the first and second joints 45, 47 and the spring member 49 are such that the flange portion 49B which has been elastically deformed or contracted during the insertion of the shaft 4707 of the second joint 47 in the circular holes 4509, 4513 and 4515 of the first joint 45 is restored to its original shape due to elastic restoring force and is snugly fitted in the intermediate circular hole 4513 to abut against the shoulder portion 4511. In this state, the surfaces 4505 and 4705 of the first and second joints 45 and 47 are flush with each other.

According to the fourth embodiment shown in FIGS. 8 and 9, in addition to the technical effects expected in the first and second embodiments, the first and second joints 45 and 47 can be coaxially held along a line by the engagement of the fourth shaft portion 4715 and the circular hole 4515 and the engagement of the first shaft portion 4709 and the circular hole 4509, and accordingly, the first and second bone pieces 1A and 1B can be accurately aligned, thus resulting in an optimal recovery of the ribs.

FIGS. 10 and 11 show a fifth embodiment of the present invention.

The first joint 55 has a bottomed hollow cylindrical body 5501 of predetermined length which is provided on the outer peripheral surface thereof with a threaded portion (male screw) 5503. The cylindrical body 5501 has an annular flat end surface 5505 which is flush with the flat end surface 1A-1 of the first bone piece 1A when the first joint 55 is fitted in the first bone piece 1A. The other end of the first joint 55 is tapered. The cylindrical body 5501 is provided on the open end thereof with a coaxial circular hole 5509 with a tapered opening 5507. The cylindrical body 5501 is also provided therein with a larger diameter circular hole (intermediate circular hole) 5513 which is connected to the small circular hole 5509 through a shoulder portion 5511, and an innermost bottomed circular hole 5515 having a predetermined length (depth) and connected to the intermediate circular hole 5513. The diameter of the innermost circular hole 5515 is smaller than the diameters of the circular holes 5513 and 5509. The circular holes 5509 and 5513 and the shoulder portion 5511 constitute an engaging portion of the first joint 55.

The second joint 57 has a circular rod body 5701 of predetermined length which is provided on the outer peripheral surface thereof with a threaded portion (male screw) 5703. The rod body 5701 has an annular flat end surface 5705 on one end on which a stepped shaft 5707 is provided. The annular flat end surface 5705 of the rod body 5701 is flush with the flat end surface 1B-1 of the second bone piece 1B when the second joint 57 is fitted in the second bone piece 1B. The other end of the rod body 5701 is conically tapered.

The stepped shaft 5707 includes a first shaft portion 5709 which is connected to the flat end surface 5705 and which can be fitted in the circular hole 5509 of the first joint, and a second shaft portion 5711 which is connected to the front end of the first shaft portion 5709 and has a diameter smaller than the first shaft portion 5709. The first shaft portion 5709 is provided on a part of the outer peripheral surface thereof with an axial recess 5713 in which a spring member 59 is provided. The spring member 59 constitutes an engaging portion of the second joint 57.

Figure 12A:
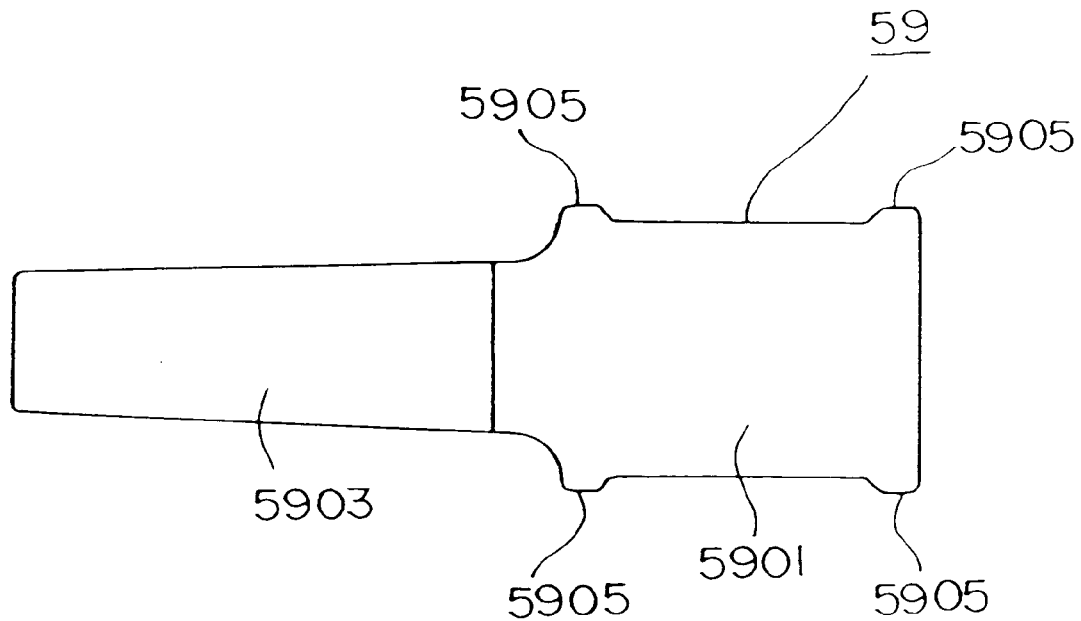
Figure 12B:
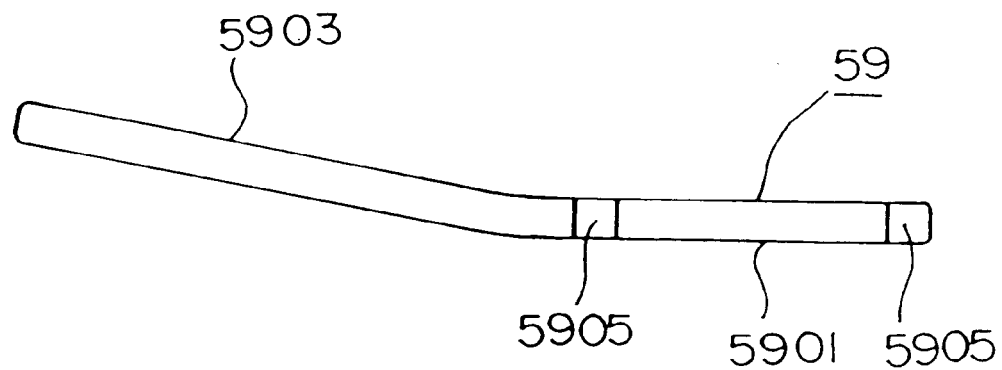

The spring member 59 includes a base plate portion 5901 which is fitted on and secured to the bottom of the recess 5713, and an oblique plate portion 5903 which extends from the base plate portion 5901 at a predetermined inclination angle. The base plate portion 5901 is provided on opposite sides thereof with projections 5905 (FIG. 12) which are snugly fitted in the recess 5713. The front end of the oblique plate portion 5903 projects out of the outer peripheral surface of the first shaft portion 5709 in the radial direction when the base plate portion 5901 is disposed on the bottom of the recess 5713.

The spring member 59 is preferably made of titanium, stainless steel, a titanium alloy, HDP (high density polyethylene), or high polymer polyethylene, etc.

The dimensions of the first and second joints 55, 57 and the spring member 59 are such that when the insertion of the shaft 5707 of the second joint 57 in the circular holes 5509, 5513 and 5515 of the first joint 55, the oblique plate portion 5903 of the spring member 59 is fitted in the circular hole 5513 of the first joint 55 and abuts against the shoulder portion 5511. In this state, the surfaces 5505 and 5705 of the first and second joints 55 and 57 are flush with each other.

According to the fifth embodiment shown in FIGS. 10 and 11, in addition to the technical effects expected in the first and second embodiments, the first and second joints 55 and 57 can be coaxially held along a line by the engagement of the second shaft portion 5711 and the circular hole 5515 and the engagement of the first shaft portion 5709 and the circular hole 5509, and accordingly, the first and second bone pieces 1A and 1B can be accurately aligned, thus resulting in an optimal recovery of the ribs.

In the first through fifth embodiments mentioned above, the first and second joints are secured to the first and second bone pieces 1A and 1B by the male threads provided on the first and second joints. The threads (screws) ensure an easy and certain connection with the bone pieces, but the connecting means is not limited to the threads (screws) in the present invention. For instance, it is possible to provide projections or the like which can be fitted in the bone pieces, on the outer peripheral surfaces of the first and second joints.

The bones to which the present invention can be applied are not limited to the ribs, and can be, for example, those of the fingers.

Although the first and second joints are made of a metal, or a ceramic, and preferably a titanium alloy and are coated with calcium phosphate compound (e.g., hydroxyapatite), the coating is not always necessary. Note that in the case that the first and second joints are coated with calcium phosphate compound, it is not necessary to coat the portions of the joints, such as the engaging portions, that are not brought into contact with the bones, since bone bonding does not take place there.

As can be understood from the above discussion, according to the present invention, the bone connector is comprised of a first joint which is embedded and secured in one of the bone pieces to be interconnected and a second joint which is embedded and secured in the other bone piece and which can be connected to the first joint. The first and second joints are made of a material strong enough to hold the cut ends of the opposed bone pieces in a close surface contact. At least the outer surfaces of the first and second joints are assimilable to the body. Consequently, in the bone connector according to the present invention, the cut ends of the bone pieces can be easily interconnected and there is no problem with the assimilation to or bioactive affinity with the body. In particular, the bone connector according to the present invention can be advantageously used to connect the cut ends of a long bone which has been cut at an intermediate portion thereof.

We claim:

1. A bone connector for reconnecting first and second cut bone pieces of a single bone, the bone connector comprising:
    a first joint including:
        a first substantially cylindrical body with a threaded outer peripheral portion for insertion, screw engaging, and securing in the cortical bone of the first cut bone piece,
        a first flat end surface adapted to be substantially flush with a cut end of the first cut bone piece,
        a stepped circular hole coaxially extending into said first substantially cylindrical body from said flat end surface along a first longitudinal direction of said first substantially cylindrical body, said stepped circular hole being formed, in order from the first flat end surface, with a coaxial hole portion having a first diameter, an intermediate hole portion having a second diameter, and an innermost first engaging portion having a predetermined length, said first diameter being smaller than said second diameter so that a boundary between the coaxial hole portion and the intermediate hole portion defines a shoulder having a surface perpendicular to the first longitudinal direction; and
    a second joint including:
        a second substantially cylindrical body with a threaded outer peripheral portion for insertion, screw engaging, and securing in the cortical bone of the second cut bone piece,
        a second flat end surface adapted to be substantially flush with a cut end of the second cut bone piece,
        a stepped shaft coaxially extending from said second substantially cylindrical body from said flat end surface along a longitudinal direction of said second substantially cylindrical body, said stepped shaft being formed, in order from the second flat end surface, with a first shaft portion for fitting into said coaxial hole portion, a second shaft portion, a third shaft portion, and a second engaging portion having said predetermined length for engaging with said innermost first engaging portion,
        an annular recess defined by said second shaft portion between said first shaft portion and said third shaft portion,
        a locking plate spring member substantially surrounding said annular recess, a portion of said locking plate spring member protruding from said annular recess,
    wherein said first substantially cylindrical body and said second substantially cylindrical body are of substantially equal diameter for connecting said first and second cut bone pieces of a single bone,
    wherein at least outer surface portions of said first and second joints are made of a material having a bioactive affinity with the human body,
    wherein said protruding portion of said plate spring member is positioned to abut said surface of said shoulder perpendicular to the first longitudinal direction for locking said first joint to said second joint and flush connecting said first flat end surface of said first joint and said second flat end surface of said second joint, and
    wherein said first and second joints are held coaxially along a line by engagement of the innermost first engaging portion and the second engaging portion and engagement of the coaxial hole portion and the first shaft portion.

2. A bone connector according to claim 1, wherein the affinity material is a calcium phosphate compound.

3. A bone connector according to claim 1, wherein said first and second joints are made of a material selected from the group consisting of titanium, stainless steel, and a titanium alloy.

4. The bone connector according to claim 3, wherein said first and second joints are coated with a material having an affinity with the human body.

5. The bone connector according to claim 1, said plate spring member comprising a cylindrical portion and a flange portion, said cylindrical portion being received within said annular recess and said flange portion extending from said annular recess for engagement with said shoulder.

6. The bone connector according to claim 5, said plate spring member further comprising a slit extending through said cylindrical portion and through said flange portion.

7. The bone connector according to claim 1, said plate spring member being made of a material selected from the group consisting of titanium, stainless steel, a titanium alloy, high density polyethylene and high polymer polyethylene.

8. The bone connector according to claim 1, said circular hole further including a tapered portion between said first flat end surface and said coaxial hole portion defining a transition between said first flat end surface and said coaxial hole portion of said circular hole, said tapered portion tapering from a diameter larger than said protruding portion of said plate spring member down to said first diameter for deforming said plate spring member to pass said coaxial hole portion upon insertion of said second joint into said first joint.

9. The bone connector according to claim 1, wherein linear movement of said first and second joints towards one another is sufficient to engage said stepped shaft with said circular hole.

10. The bone connector according to claim 1, said material having an affinity with the human body comprising apatite.

11. A bone connector for reconnecting first and second cut bone pieces of a single bone, the bone connector comprising:
    a first joint including:
        a first substantially cylindrical body with a threaded outer peripheral portion for insertion, screw engaging, and securing in the cortical bone of the first cut bone piece, a first flat end surface adapted to be substantially flush with a cut end of the first cut bone piece, a stepped circular hole coaxially extending into said first substantially cylindrical body from said flat end surface along a first longitudinal direction of said first substantially cylindrical body, said stepped circular hole being formed, in order from the first flat end surface, with a coaxial hole portion having a first diameter, an intermediate hole portion having a second diameter, and an innermost first engaging portion having a predetermined length, said first diameter being smaller than said second diameter so that a boundary between the coaxial hole portion and the intermediate hole portion defines a shoulder having a surface perpendicular to the first longitudinal direction; and a second joint including:
  a second substantially cylindrical body with a threaded outer peripheral portion for insertion, screw engaging, and securing in the cortical bone of the second cut bone piece,
  a second flat end surface adapted to be substantially flush with a cut end of the second cut bone piece,
  a stepped shaft coaxially extending from said second substantially cylindrical body from said flat end surface along a longitudinal direction of said second substantially cylindrical body, said stepped shaft being formed, in order from the second flat end surface, with a first shaft portion for fitting into said coaxial hole portion, an intermediate shaft portion, and a second engaging portion having said predetermined length for engaging with said innermost first engaging portion,
  a recess defined in said intermediate shaft portion,
  a locking plate spring member positioned within said recess, a portion of said locking plate spring member extending from said recess, wherein said first substantially cylindrical body and said second substantially cylindrical body are of substantially equal diameter for connecting said first and second cut bone pieces of a single bone, wherein at least outer surface portions of said first and second joints are made of a material having a bioactive affinity with the human body, wherein said extending portion of said plate spring member is positioned to abut said surface of said shoulder perpendicular to the first longitudinal direction for locking said first joint to said second joint and flush connecting said first flat end surface of said first joint and said second flat end surface of said second joint, and wherein said first and second joints are held coaxially along a line by engagement of the innermost first engaging portion and the second engaging portion and engagement of the coaxial hole portion and the first shaft portion.

12. The bone connector according to claim 11, said plate spring member being made of a material selected from the group consisting of titanium, stainless steel, a titanium alloy, high density polyethylene and high polymer polyethylene.

13. The bone connector according to claim 11, said circular hole further including a tapered portion between said first flat end surface and said coaxial hole portion defining a transition between said first flat end surface and said coaxial hole portion of said circular hole, said tapered portion tapering from a diameter larger than said extending potion of said plate spring member down to said first diameter for deforming said plate spring member to pass said coaxial hole portion upon insertion of said second joint into said first joint.

14. The bone connector according to claim 11, said plate spring member comprising a base plate fitted in and secured to a bottom surface of said recess, said extending portion of said plate spring member comprising an obliquely projecting portion extending from said base portion at a predetermined inclination angle.

15. The bone connector according to claim 14, said base plate including a plurality of projections on opposite sides of said base plate, said projections engaged in said recess.

16. The bone connector according to claim 11, wherein linear movement of said first and second joints towards one another is sufficient to engage said stepped shaft with said circular hole.

17. The bone connector according to claim 11, wherein said stepped shaft is configured to be engaged with said circular hole when said first and second joints are fully screw engaged into the first and second cut bone pieces, so as to be substantially flush therewith.

18. The bone connector according to claim 11, said material having bioactive affinity comprising a calcium phosphate compound.

19. The bone connector according to claim 11, said first and second joints made of a material selected from the group consisting of titanium, stainless steel and titanium alloys.

20. The bone connector according to claim 19, said first and second joints coated with a material having an affinity with the human body.

21. The bone connector according to claim 20, said material having an affinity with the human body comprising apatite.

* * * * *

UNITED STATES PATENT AND TRADEMARK OFFICE
CERTIFICATE OF CORRECTION

PATENT NO. : 6,001,103
DATED : December 14, 1999
INVENTOR(S) : S. Hitomi, et. al.

It is certified that error appears in the above-indentified patent and that said Letters Patent is hereby corrected as shown below:

Title page, item [54] and col. 1, should read as follows:
-- Bone Connector Having Coaxial Engagement for Joining Cut Bone Ends --.

Signed and Sealed this

Twentieth Day of March, 2001

Attest:

NICHOLAS P. GODICI

Attesting Officer     Acting Director of the United States Patent and Trademark Office